United States Patent [19]

Mittelmeier et al.

[11] Patent Number: 4,516,276
[45] Date of Patent: May 14, 1985

[54] BONE SUBSTITUTE AND A METHOD OF PRODUCTION THEREOF

[75] Inventors: Heinz Mittelmeier, Homburg-Schwarzenbach, Fed. Rep. of Germany; Heinz Moser, Selzach; Beat Leu, Ipsach, both of Switzerland

[73] Assignee: Oscobal AG, Selzach, Switzerland

[21] Appl. No.: 593,174

[22] Filed: Mar. 26, 1984

Related U.S. Application Data

[63] Continuation of Ser. No. 217,455, Dec. 17, 1980, abandoned.

[30] Foreign Application Priority Data

Dec. 18, 1979 [EP] European Pat. Off. ........ 79810183.8

[51] Int. Cl.$^3$ .................. A61F 1/00; A61F 1/24
[52] U.S. Cl. .................... 3/1.91; 128/92 C; 128/92 G
[58] Field of Search .............. 3/1.9, 1.91, 1; 128/92 C, 92 D, 92 G

[56] References Cited

U.S. PATENT DOCUMENTS

| 3,523,807 | 8/1970 | Gerendas . | |
|---|---|---|---|
| 3,767,437 | 10/1973 | Cruz, Jr. | 3/1.9 UX |
| 3,849,805 | 11/1974 | Leake et al. | 128/92 C X |
| 4,051,598 | 10/1977 | Sneer | 3/1.9 UX |
| 4,064,567 | 12/1977 | Burstein et al. . | |
| 4,131,597 | 12/1978 | Bluethgen et al. | 128/92 C X |
| 4,309,488 | 1/1982 | Heide et al. | 3/1.9 X |

FOREIGN PATENT DOCUMENTS

| 0018496 | 11/1980 | European Pat. Off. . |
| 2022498 | 12/1970 | Fed. Rep. of Germany . |
| 2350826 | 12/1977 | France . |
| 2374040 | 7/1978 | France . |
| 2410477 | 6/1979 | France . |

Primary Examiner—Ronald L. Frinks
Attorney, Agent, or Firm—Wender Murase & White

[57] ABSTRACT

A bone substitute comprised of collagen material in the form of fleece or a spatial meshwork having apatite, the mineral component of bone material, admixed therewith. The structure of the collagen material may be strengthened by carbohydrate or starch or may be applied, in the form of a coating, to a honeycomb-like basic structure made from a variety of materials.

Such a bone substitute has a good support quality, promotes bone growth and also has a good styptic or haemostatic effect.

8 Claims, No Drawings

2

BONE SUBSTITUTE AND A METHOD OF PRODUCTION THEREOF

This is a continuation of application Ser. No. 217,455, filed Dec. 17, 1980, now abandoned.

FIELD OF THE INVENTION

The present invention relates to a bone substitute and a method of production thereof.

In orthopaedics, there are numerous complaints and/or injuries which lead to skeletal defects. To overcome these defects, a bone substitute is required. Thus, for example, the defects may be caused as a result of non-malignant cystic tumors which may lead to excessively large cavities in the bone with the risk of spontaneous fractures, bone defects after resection of malignant tumors, bone gaps after extension osteotomy and defect pseudoarthroses or as a result of obtaining extended stiffening of the spine.

DESCRIPTION OF THE PRIOR ART

As a bone substitute, autologous bone material has, hitherto proved to be the most suitable. The bone material is removed from a different part of the body of the patient, such as the pelvis or shinbone and is transplanted into the region of the defect. Autologous bone material has the major advantage that as individually identical albumen it may be rapidly implanted without setting up any immunological rejection reaction. On the other hand, autologous bone material has the disadvantage that a further wound is formed which additionally strains the patient biologically, for example, due to loss of blood, and may even cause a defect in the region from which the material is removed. The wound thus caused may only heal slowly and may itself cause structural weakness in the skeletal portion from which the material has been removed.

For this reason, attempts have been made to employ homoioplastics, whereby bone material from different humans is used. The bone material may, in fact, be obtained from corpses. The bone material may be preserved, until it is required for use, in sterile saline solutions, such as Zialite or may be deep frozen. In homoioplastics, it is an identical, but individually different, albumen which leads to certain immunological rejection reactions. Consequently, homoioplastics do not have such a good osteoplastic effect as autologous material. This material does stimulate bone regeneration but this is prevented by the necessary biological synthesis of the transplant. Moreover, the obtaining and storage of such material in a sterile form poses difficulties for the clinics and hospitals concerned. Moreover, legal problems may well arise in connection with organ removal from corpses.

For a long time, it has also been attempted to use bone material obtained from animals, this being a ready source. However, the unrelated type of albumen found in this heteroplastic leads to greater immunological rejection reactions with rejection or encapsulation of the transplant and only gives rise to sparse stimulation of bone regeneration.

It is, however, also known to use heteroplastics, such as animal bone material in the form of bone splinters or dust or bone meal (Corticalis and Spongiosa), particularly that obtained from calves. In this case, the albumenic substances of the bone marrow are washed out and the bone is degresed and dealbumenized. However, the material still contains a certain amount of collagen and apatite. The material, known by the name "Kieler Knochenspan" has not, however, successfully been used and, at present, autologous or homologous bone substitutes are usually used.

SUMMARY OF THE INVENTION

The present invention seeks to provide a bone substitute which may be produced on an industrial scale at a uniform quality and having satisfactory sterility, whilst avoiding the disadvantages associated with autologous or homologous bone substitutes. However, the invention also seeks to provide a bone substitute which stimulates natural bone development better than heterologous bone substitutes.

According to the present invention, there is provided bone substitute comprising a mixture of spatial structured collagen and the mineral component of bone material, namely apatite.

Also according to the present invention there is provided a method of producing such a bone substitute wherein the collagen material is uniformly mixed with apatite powder or granules.

DESCRIPTION OF THE PREFERRED EMBODIMENTS

For a long time, clinics have used styptic material in the form of collagen fleeces. Collagen is used herein to mean the supporting albumen of the connective tissues, skin, sinews and bones. Thus, a chemical distinction is made between neutral salt and acid-soluble collagen and a more-or-less insoluble collagen fibre in which the collagen molecules are strongly bonded.

The chemical collagen unit has a high molecular weight of about 300,000. This macromolecular peptide is formed of three helical protein chains, each having a molecular weight of approximately 95,000. The collagen is predominantly obtained from animal skin and, in its correct composition or formulation, causes immediate blood coagulation and hence is very useful for closing wounds. Accordingly, the use of this material is indicated in connection with injuries to organs such as, for example, the liver, and for covering burn wounds or wounds which granulate. In individual cases, the collagen material has been used as a bone substitute in jawbone surgery, but there are contrasting opinions regarding the success of such surgery. In those cases where the bone substitute is used in so-called "strong" mountings, such as within a bone cavity and in smaller gaps, both negative and also positive results have been given. In the case of so-called "weak" mountings, such as when the substitute material has to be implanted in a soft tissue gap after complete bone resection, no noticeable success has been achieved using collagen fibres. In orthopaedic surgery, however, it would therefore be desirable to have an effective bone-forming material for use in the so-called "weak" mounting.

To obtain a bone substitute which is bone-forming in both of the above types of mounting and which is universally applicable, it is necessary to add substances to the collagen fleece which cause or promote this effect. A substance which is particularly suitable for this purpose is the mineral component of paraplastic bone substances, namely apatite, which is predominantly hydrated tricalcium phosphate. From many prior experiments, it is already known that apatite has a substantial bone development effect. An essential feature of such material is that it occurs in particularly porous forms in order to promote the substitution of this material through vital bone tissue.

It is therefore stressed that the styptic effect of the collagen fleece is desirable. During bone operations, heavy bleeding occurs, in most cases, from the fine bone passages and from the blood vessels in distinction from the soft part tissue, cannot there be sealed off by electrocoagulation. Added to this is the fact that the styptic effect of the collagen fleece is improved by the apatite addition, since the apatite-calcium ions are liberated and calcium ions play a substantial part in the coagulation of the blood.

The collagen material is generally obtained from animal skin, such as pigskin, by treatment to the skin with proteolytic enzymes. Subsequently, the material is cleansed, lyophilized and sterilized utilizing gammaradiation. For certain purposes, however, it may be necessary to make the collagen material from human tissue. This is particularly true for transplant purposes.

Preferably, the collagen material is first produced in the form of a pressed fleece grid or network or in a plaited, knitted or woven textile form or as spatial mesh or honeycomb grid, similar to the natural spongiosa structure. When producing a fleece network, the fleece layer may pass through a screen press roller by means of which grid a pattern is impressed therein. When producing the bone substitute, it is necessary to ensure that as thorough mixing as possible of the collagen material with the apatite powder or granules is achieved so as to produce a uniform product. Two different methods of doing this may be used.

Firstly, the collagen fleece may be produced in two thin layers and is then dusted with apatite powder or granules. The mixture is subjected to a pressing operation by passing it through a pair of rollers which cause the apatite powder to be pressed into the mesh of the fleece. This method may be carried out in either dry or wet conditions.

Alternatively, the collagen fibre material may be mixed with apatite powder or granules in a suitable mixture before being formed into layers and dried. In natural bone tissue, the ratio of collagen to apatite is approximately 1:1, but in a bone substitute according to the present invention, these proportions may be varied within a wide range dependent upon its ultimate intended use. The material preferably has suitable antibiotics admixed therewith, which are particularly important in septic bone surgery. The end product may be produced in the form of granules, amorphous or shaped sections, chips, strips or tubes. It is also possible to give the material the shape of natural human bones.

Collagen fleece material produced by conventional methods is generally very soft, which makes it possible for the material to be forced into bone cavities and apertures so that it readily abuts against the natural bone surface or is pressed thereagainst. This, however, is not desirable in the case where bridges to correct a defect have to be provided so as to have a certain pre-determined strength. It is therefore desirable to reinforce the structure of the collagen fleece. For this carbohydrate starch or fibrin may be used. To strengthen the structure still further, the collagen material-apatite mixture may also be applied in the form of a coating onto honeycomb-like basic structures, the structures themselves being formed from plastics materials, textiles, metal, aluminium oxide, ceramics, carbon-fibre fabrics, carbon or bone cement as desired. The structures may also be given the shape of the bone section which they are to replace.

We claim:

1. A bone substitute consisting essentially of a mixture of collagen fleece with apatite in the form of powder or granules, wherein the collagen is present in the form of an enzymatically treated, cleansed, lyophilized and sterilized collagen fleece.

2. A bone substitute according to claim 1, additionally containing fibrin as a strengthening agent for said collagen fleece.

3. A bone substitute according to claim 1, in the form of a coating applied to a honeycomb-like basic structure.

4. A bone substitute according to claim 3, wherein the honeycomb-like basic structure is made from a material selected from the group consisting of plastics materials, textiles, metals, ceramics, carbon fibre fabrics and carbon or bone cement.

5. A bone substitute according to claim 1 having the shape of natural bones.

6. A bone substitute according to claim 1 additionally containing antibiotics.

7. A method of producing a bone substitute material, wherein said material consists essentially of a mixture of collagen fleece and apatite, and wherein said collagen fleece is present in the form of enzymatically treated, cleansed, lyophilized and sterilized collagen fleece, comprising the steps of forming a thin layer of collagen fleece, dusting said collagen fleece with apatite powder or granules, and subsequently pressing the apatite-dusted collagen fleece to cause the apatite to be pressed into said collagen fleece.

8. A method of producing a bone substitute material, wherein said material consists essentially of a mixture of collagen fleece and apatite, and wherein said collagen fleece is present in the form of enzymatically treated, cleansed, lyophilized and sterilized collagen fleece, comprising the steps of mixing said collagen fleece with apatite powder or granules, forming said mixture into a predetermined configuration and drying said formed mixture.

* * * * *